United States Patent
Alcantar et al.

(10) Patent No.: US 10,934,453 B2
(45) Date of Patent: Mar. 2, 2021

(54) CUTIN-LIKE MATERIALS WITH ADVANCED FUNCTIONALITIES AND METHODS OF MANUFACTURE

(71) Applicants: Norma Arcelia Alcantar, Tampa, FL (US); Ryan Gates Toomey, Tampa, FL (US); Fei Guo, Tampa, FL (US); Zeinab Veisi, Tampa, FL (US); Tunan Peng, Odessa, FL (US)

(72) Inventors: Norma Arcelia Alcantar, Tampa, FL (US); Ryan Gates Toomey, Tampa, FL (US); Fei Guo, Tampa, FL (US); Zeinab Veisi, Tampa, FL (US); Tunan Peng, Odessa, FL (US)

(73) Assignee: University of South Florida, Tampa, FL (US)

(*) Notice: Subject to any disclaimer, the term of this patent is extended or adjusted under 35 U.S.C. 154(b) by 246 days.

(21) Appl. No.: 16/280,207

(22) Filed: Feb. 20, 2019

(65) Prior Publication Data

US 2019/0177571 A1    Jun. 13, 2019

Related U.S. Application Data

(60) Division of application No. 15/783,226, filed on Oct. 13, 2017, now Pat. No. 10,253,208, which is a continuation of application No. PCT/US2016/027315, filed on Apr. 13, 2016.

(60) Provisional application No. 62/146,591, filed on Apr. 13, 2015.

(51) Int. Cl.
| | | |
|---|---|---|
| *C09D 167/00* | (2006.01) | |
| *C09D 167/04* | (2006.01) | |
| *A61K 36/33* | (2006.01) | |
| *C09D 7/61* | (2018.01) | |
| *C08G 63/60* | (2006.01) | |
| *C08G 63/68* | (2006.01) | |
| *C08K 3/08* | (2006.01) | |
| *C08K 3/34* | (2006.01) | |
| *C08K 3/36* | (2006.01) | |

(52) U.S. Cl.
CPC ............ *C09D 167/04* (2013.01); *A61K 36/33* (2013.01); *C08G 63/60* (2013.01); *C08G 63/681* (2013.01); *C09D 7/61* (2018.01); *C08K 3/08* (2013.01); *C08K 3/34* (2013.01); *C08K 3/36* (2013.01); *C08K 2003/0831* (2013.01); *C08K 2003/0856* (2013.01)

(58) Field of Classification Search
None
See application file for complete search history.

(56) References Cited

U.S. PATENT DOCUMENTS

2008/0262190 A1* 10/2008 Koskimies .............. C07C 67/03
528/271

* cited by examiner

*Primary Examiner* — Stefanie J Cohen
(74) *Attorney, Agent, or Firm* — Michele L. Lawson; Smith & Hopen, P.A.

(57) ABSTRACT

Cutin-based devices, coatings and methods of producing such devices and coatings are presented herein. Cutin-like materials (CLMs) are presented which mimic and adapt coatings found in nature for the next generation of functional coatings. Cutin has several advantages including excellent UV resistance, natural resistance to bacteria and viruses, noncorrosive, and stability under abrupt changes in temperature and environment. CLMs can be engineered at the nanoscale and readily impregnated with metals and metal oxides materials.

10 Claims, 7 Drawing Sheets

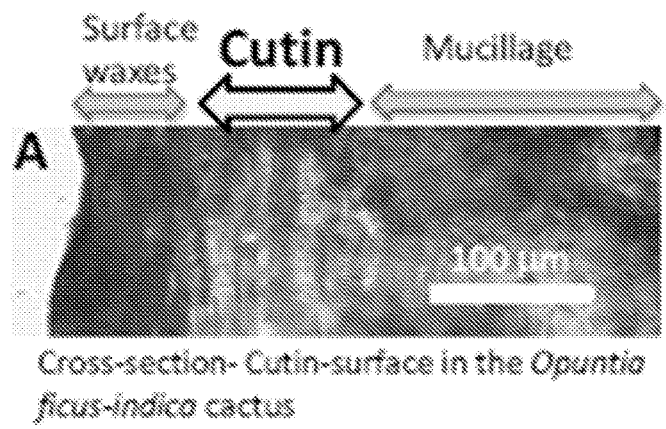
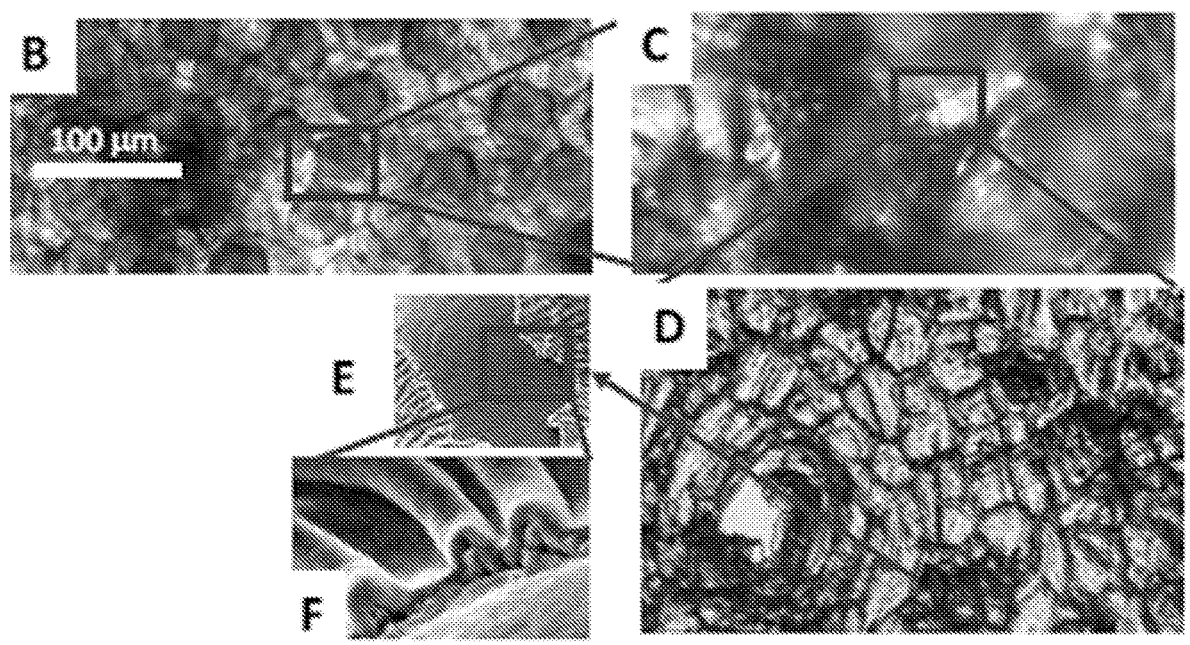
Fig. 3A-F

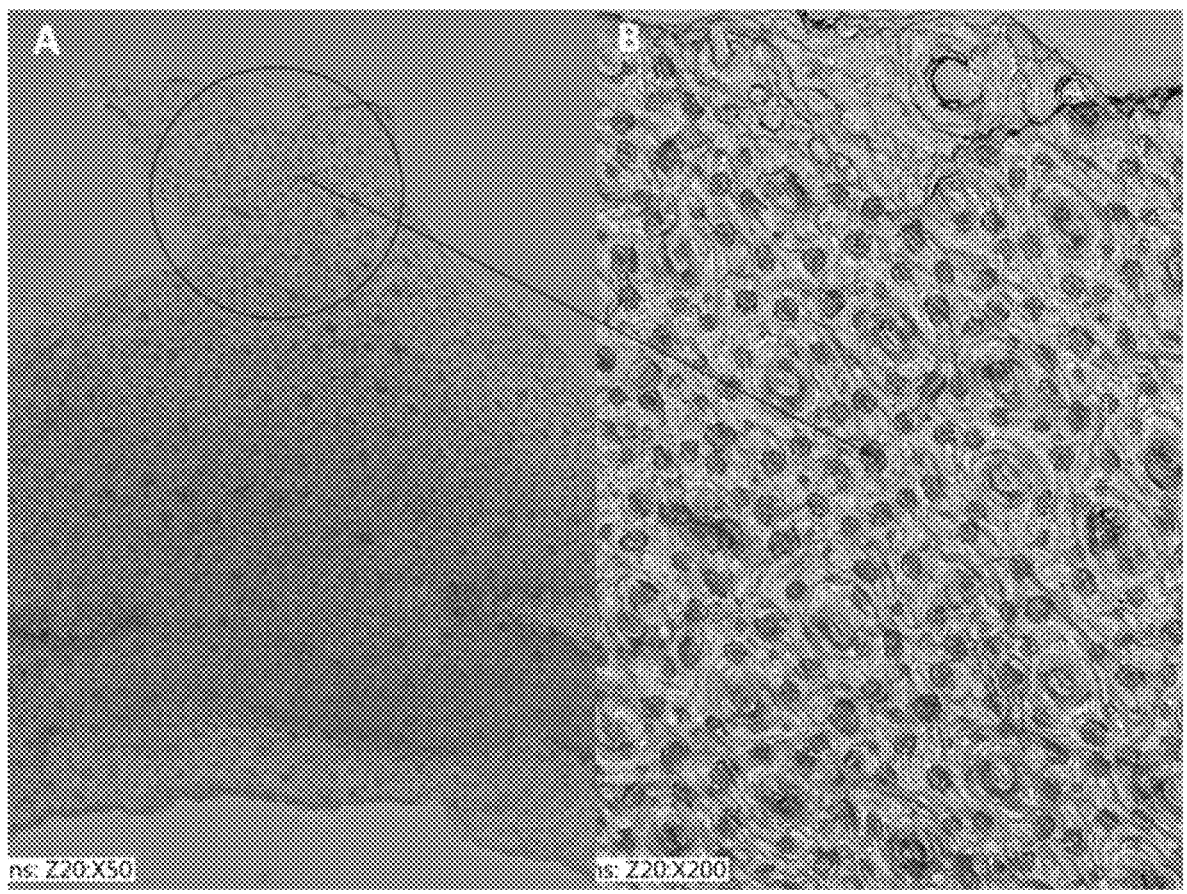
Fig. 4A-B

CUTIN-LIKE MATERIALS WITH ADVANCED FUNCTIONALITIES AND METHODS OF MANUFACTURE

CROSS REFERENCE TO RELATED APPLICATIONS

This application is a division of and claims priority to currently pending U.S. Nonprovisional application Ser. No. 15/783,226, entitled: "Cutin-Like Materials with Advanced Functionalities and Methods of Manufacture", filed on Oct. 13, 2017, now U.S. Pat. No. 10,253,208, which is a continuation of and claims priority to International Patent Application No. PCT/US2016/027315, filed Apr. 13, 2016, which claims priority to U.S. Provisional Patent Application No. 62/146,591, entitled: "Using the Skin of the Cactus for Making Cutin-Like Materials with Advanced Functionalities", filed Apr. 13, 2015, the entire contents of each of which is herein incorporated into this disclosure.

FIELD OF INVENTION

This invention relates cutin-based devices, methods of use and methods of manufacturing such devices. More specifically, the present invention provides for chemical alteration of cutin for use in development of devices.

BACKGROUND OF THE INVENTION

Cutin, the structural component of the plant cuticle, is a polyester. Natural cutin polymeric arrays are found in the outer surfaces of leaves and shoots of plants. In natural processes, cutin, a non-living substance, results from the polymerization of fatty acids in the presence of oxygen.

Cutin is the major constituent (between 40% and 80% of weight) of the cuticle and is defined as a polymeric network of oxygenated $C_{16}$ and $C_{18}$ fatty acids cross-linked by ester bonds. Specifically, cutin is a polyester composed of ω-hydroxy-$C_{16}$ and $C_{18}$ fatty acids, dihydroxy-$C_{16}$ acid, 18-hydroxy-9,10-epoxy-$C_{18}$ acid and 9,10,18-trihydroxy-$C_{18}$ acid. Cutin can be depolymerized by cleavage of the ester bonds by alkaline hydrolysis, transesterification and other methods. These chemical methods yield monomers and/or their derivatives depending on the reagent used. The 9- or 10,16-dihydroxyhexadecanoic acid and 16-hydroxyhexadecanoic acid are the major components of the $C_{16}$ cutins. Only in some cases, 16-hydroxy-10-oxo-$C_{16}$ acid and 16-oxo-9 or 10-hydroxy $C_{16}$ acid are monomers. Major components of the $C_{18}$ family of monomers are 18-hydroxy-9,10-epoxyoctadecaonoic acid and 9,10,18-trihydroxyoctadecanoic acid together with their monounsaturated homologues. Generally, cutin polyester is held together by primary alcohol ester linkages with about half of the secondary hydroxyl groups involved in ester cross-links (Heredia, A. 2003)

In the cuticle of some plant species, once all the wax and cutin components have been removed, there is some remaining residual material. This depolymerization-resistant residue is believed to represent cutin monomers held together by nonester bonds and is termed cutan. While the cuticles of some plant species appear to completely lack cutans, in a number of species, the two biopolymers, cutin and cutan, may occur in varying ratios according to their relative abundance at different stages of cuticle development. (Heredia, A. 2003)

Heredia-Guerrero et al. have synthesized a memetic polymer of plant cutin from 9,10,16-trihydroxyhexadecanoic (aleuritic) acid through a low temperature polycondensation reaction. In this synthetic polymer, the polyaleurate framework was found to be more rigid than natural cutin having additional larger short-range ordered domains and displaying slightly different mechanical properties with respect to natural cutin due to additional hydrogen bonding within the framework of polyaleurate. (Heredia-Guerrero, J. A. et al., 2009)

Essential synthetic issues associated with the production of cutin in plants have been studied in botany and plant lipid biochemistry. (Franke, R. et al., 2005; Li, Y. et al., 2007; Li-Beisson, Y. et al., 2009; Panikashvili, D. et al., 2010; Pollard, M. et al., 2008; Riederer, M. et al., 1993) In some instances, these fields recognized different derivatives of cutin monomers with individual names. For instance, cutan is a non-hydrolysable aliphatic biopolyester found in the *Agave americana*. (Gupta, N. et al., 2006) Suberin, which is also derived from cutin monomers found in *Cereus peruvianus* cacti, is synthesized from aliphatic and phenolic polyesters. (Franke, R. et al., 2007; Kim, Y. H. et al., 2002) Cacti also have surface waxes formed by epicuticular lipids which are randomly structured. (Maiti, R. K. et al., 2003; Rezanka, T. et al., 1998)

In particular, the composition of cutin found in the outer layer of cactus pads and shoots is of interest in 2-D layered technology development. Cactus epidermis and cuticles are capable of withstanding UV radiation damage over long periods of time (>100 years), and they tolerate relatively high and low temperatures, endure abrupt changes of temperature, withstand water damage, and reflect light. (Drezner, T. D., 2008) Natural cutin surfaces are extremely stable, as they do not crack nor corrode like other synthetic materials under the same extreme weather conditions. Moreover, cutin-like materials can be engineered to be amorphous or crystalline and readily impregnated with metals and metal oxides materials. If crystalline surfaces are wanted, the polyesters are aligned before curing in crystallographic configurations by using shearing forces or conditions for self-assembly. This leads to regions where the polymers are ordered in a specific direction. If amorphous materials are wanted, the polyesters are cured after being mixed. This leads to regions with random configurations.

SUMMARY OF THE INVENTION

Sustainable material synthesis with advanced properties is key to robust, functional coatings for large-scale aircraft infrastructure, flexible electronic devices and bio-controlled instrumentation. The inventors have engineered and characterized two-dimensional arrays of cutin-like materials (CLM) for the next generation of functional coatings.

In an embodiment, a coating is presented comprising naturally derived or synthetic cutin-like materials (CLM) containing fatty acid iron salts, metals, and dielectric materials. The metals can be selected from the group consisting of iron (Fe) and gold (Au). The dielectric materials can be selected from the group consisting of silicon dioxide ($SiO_2$) and silicon nitride ($Si_3N_4$). The coating may be derived from cutin found in cacti species selected from the group consisting of *Opuntia ficus-indica, Agave Americana, Cereus peruvianus*, and *Rhipsalis* species. In some embodiments, the CLM is derived from a non-hydrolysable aliphatic biopolyester found in the *Agave americana*, or monomers found in *Cereus peruvianus* cacti. The coating can be comprised of randomly structured epicuticular lipids.

In another embodiment, a cutin-like material (CLM) is presented comprising CLM precursors; substituted ω-hydroxyl fatty acids; and fatty acid iron salts. The CLM precursors can be $C_{12}$-$C_{20}$ aliphatic fatty acids and can be derived from cutin found in cacti species selected from the group consisting of *Opuntia ficus-indica, Agave Americana, Cereus peruvianus*, and *Rhipsalis* species. The CLM can be modified with metals and metal oxides to create enriched nanolayers.

A method of manufacturing cutin-like materials (CLM) for use in two-dimensional coatings and three-dimensional structures is also presented comprising providing CLM precursors in a solution; adding substituted ω-hydroxyl fatty acids to the solution; adding glycerol or ferulate to the solution; and adding an acid or base to the solution to catalyze a reaction between the oxygen donor groups, the glycerol and the CLM precursors. The CLM precursors can be naturally derived from cutin found in cacti species selected from the group consisting of *Opuntia ficus-indica, Agave Americana, Cereus peruvianus*, and *Rhipsalis* species. Alternatively, the CLM precursors can be synthetically derived. The CLM precursors can be $C_{12}$-$C_{20}$ aliphatic fatty acids linked together via esterification to result in large areas of simple CLM. Fatty acid iron salts can be incorporated into the solution to tailor electronic sensitivity. Metallic, such as iron and gold, and dielectric materials, such as silicon oxide ($SiO_2$) and silicon nitride ($Si_3N_4$), can be incorporated into the solution to enhance surface reactivity and reflecting properties of the CLM.

BRIEF DESCRIPTION OF THE DRAWINGS

For a fuller understanding of the nature and objects of the invention, reference should be made to the following detailed description, taken in connection with the accompanying drawings, in which:

FIG. 3A-F is a series of images depicting natural cutin: The 3 top images (FIGS. 3A, B, C) are from the cuticle of the *Opuntia ficus indica*. The lower right picture also corresponds to cutin for OFI (FIG. 3D). The small lower left images were taken from the epidermis of *Rhipsalis op*. at high mag. (FIGS. 3E & F). The wrinkles are surface waxes. The smooth region shows cutin nanolayers.

FIG. 4A-B are a series of images depicting the sublayer of the natural cactus skin from the *Opuntia ficus-indica, OFI*, species. A) 50× magnification; B) 200× magnification. In the higher magnification picture (B) one can observe two regions. First the dark spots showed denser areas of small weight polyesters. The lighter regions are polyesters of higher molecular weight arranged in a fibril configuration to maintain the aggregates evenly spaced.

DETAILED DESCRIPTION OF THE PREFERRED EMBODIMENT

Figure 1:
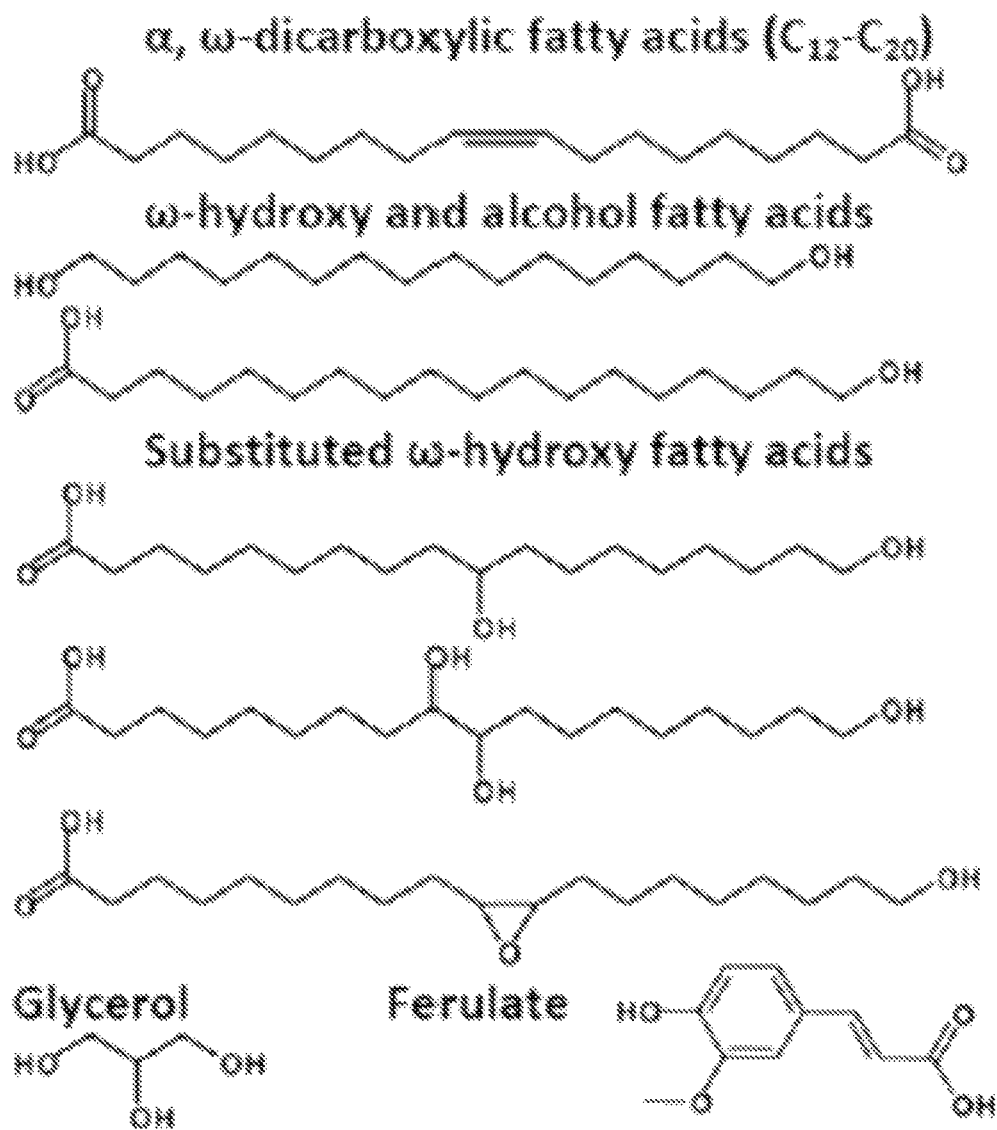
FIG. 1 is an image depicting the precursor groups for CLM.

As used herein, the singular forms "a," "an" and "the" include plural referents unless the context clearly dictates otherwise. Thus, for example, reference to "a polypeptide" includes a mixture of two or more polypeptides and the like.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

As used in the specification and claims, the singular form "a", "an" and "the" include plural references unless the context clearly dictates otherwise.

As used herein, "about" means approximately or nearly and in the context of a numerical value or range set forth means ±15% of the numerical value.

The term "polymer" as used herein refers to a relatively high molecular weight organic compound, natural or synthetic, whose structure can be represented by a repeated small unit, the monomer. Synthetic polymers are typically formed by addition or condensation polymerization of monomers.

The term "monomer" as used herein refers to a molecule of relatively low molecular weight that is capable of reacting with identical or different molecules of low molecular weight to form a polymer.

The term "cutin" as used herein refers to a waxy waterproof substance, consisting of derivatives of fatty acids as well as possible soaps and resinous materials. Natural cutin is the main constituent of the cuticle of plants. Synthetic cutin can be manufactured using cutin precursors or monomers. Cutin or cutin-like material (CLM) is the general structural unit of the 2-D layered materials described herein.

The term "cutin-like material (CLM)" as used herein refers to both natural cutin that has been extracted from a cacti plant as well as synthetic cutin that has been synthesized according to specifications. CLM exhibits the hydrophobic properties of cutin and can be made into coatings, laminates and large arrays as well as devices.

The term "coating" as used herein refers to at least one layer of a CLM that is placed over at least a portion of the surface of a substrate.

The term "natural" as used herein refers to a product existing in nature. In particular, "natural" refers to cutin biopolyesters, monomers, extracted from a plant species for use in manufacturing a CLM. In some embodiments, the plant species is a cacti species. "Naturally derived" refers to use of some form of a product that was originally found in nature. For example, in some embodiments, the CLM precursors are extracted from cutin that is found in plants.

The term "synthetic" or "synthetically derived" as used herein refers to a product produced artificially by human hand by chemical synthesis. In particular, "synthetic" refers to the manufacture of a product which mimics a natural product. In some embodiments, CLM are chemically synthesized to mimic natural cutin.

The inventors present herein extract and/or synthetic methodologies as well as characterize and engineer two-dimensional arrays of cutin-like materials (CLM) for the next generation of functional coatings that go beyond materials such as graphene and other inorganics. Aldolase-Catalyzed Condensation reactions are followed to construct specific polysaccharides scaling from 0.01 to 1 mol to mimic the properties of those from the OFI extracts. In this method, aldolase enzymes are combined with ferulate and glycerol as one substrate. Those surfaces are exposed to judicious compositions of myriad aldehydes molecules to be able to reconstruct glycan using block-by-block assembly until the desired structure is achieved. The advantage for using this type of reactions is the ability to control stereochemistry for each polyester block.

Sustainable material synthesis is accomplished by mimicking nature's ability to create the primary aerial surface of cactus plants with one of nature's largest two-dimensional biological interfaces to produce novel, functionalized materials. The synthesis of cutin templates both aliphatic and aromatic involves C12, C14, C16, C18, and C20 substituted, ω-hydroxy and ω-hydroxy-epoxy unsaturated fatty acids and glycerol. Variations of structure and chemical, mechanical and electrical functionality are studied by incorporating other groups such as α, ω dicarboxylic acids, fatty alcohols, and ferulate (FIG. 1). Both synthetic (i.e., commercially available) and naturally extracted cutin precursors are studied. Ester-bond hydrolysis and transesterification of cuticles from *Opuntia ficus-indica* cacti (i.e., OFI or prickly pear) and *Rhipsalis* species (common succulent) yields ferulate, glycerol, and fatty acids and alcohols. Such cacti have been selected because they are abundant, need little water to growth, are extremely resilient and growth widely. Specifically, to investigate electrical properties of CLM, Synthetic fatty acid metal salts (i.e., with iron) is used as precursors in the investigation of the electrical properties of CLM. The natural production of such materials is found in the cacti species such as *Opuntia ficus-indica*, *Agave Americana*, *Cereus peruvianus*, and *Rhipsalis* species.

Figure 2:
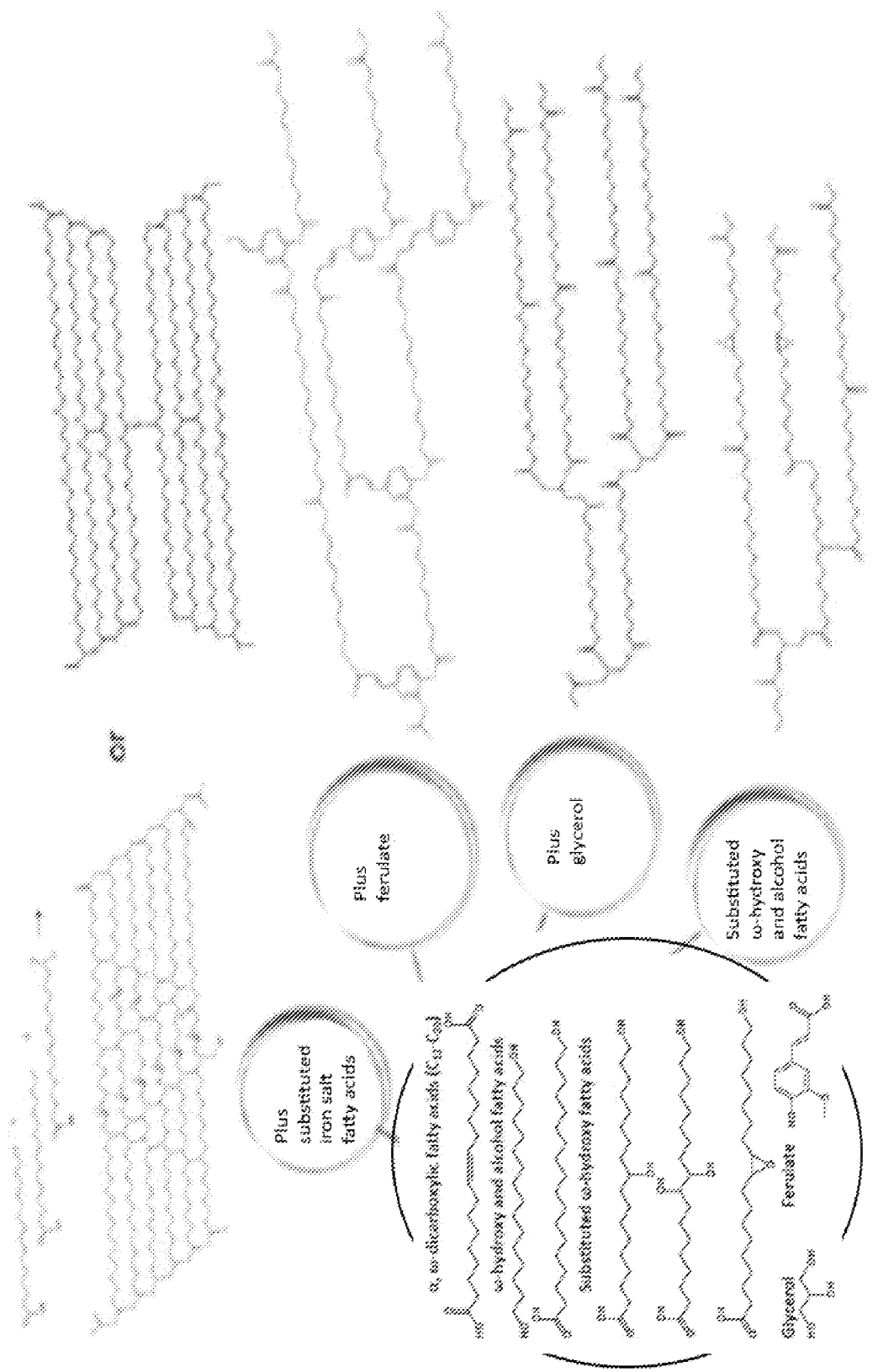
FIG. 2 is an image depicting a schematic representation of CLM compounds using pure or a mixture of cutin-like precursors from FIG. 1 interfaces.
Figure 5:
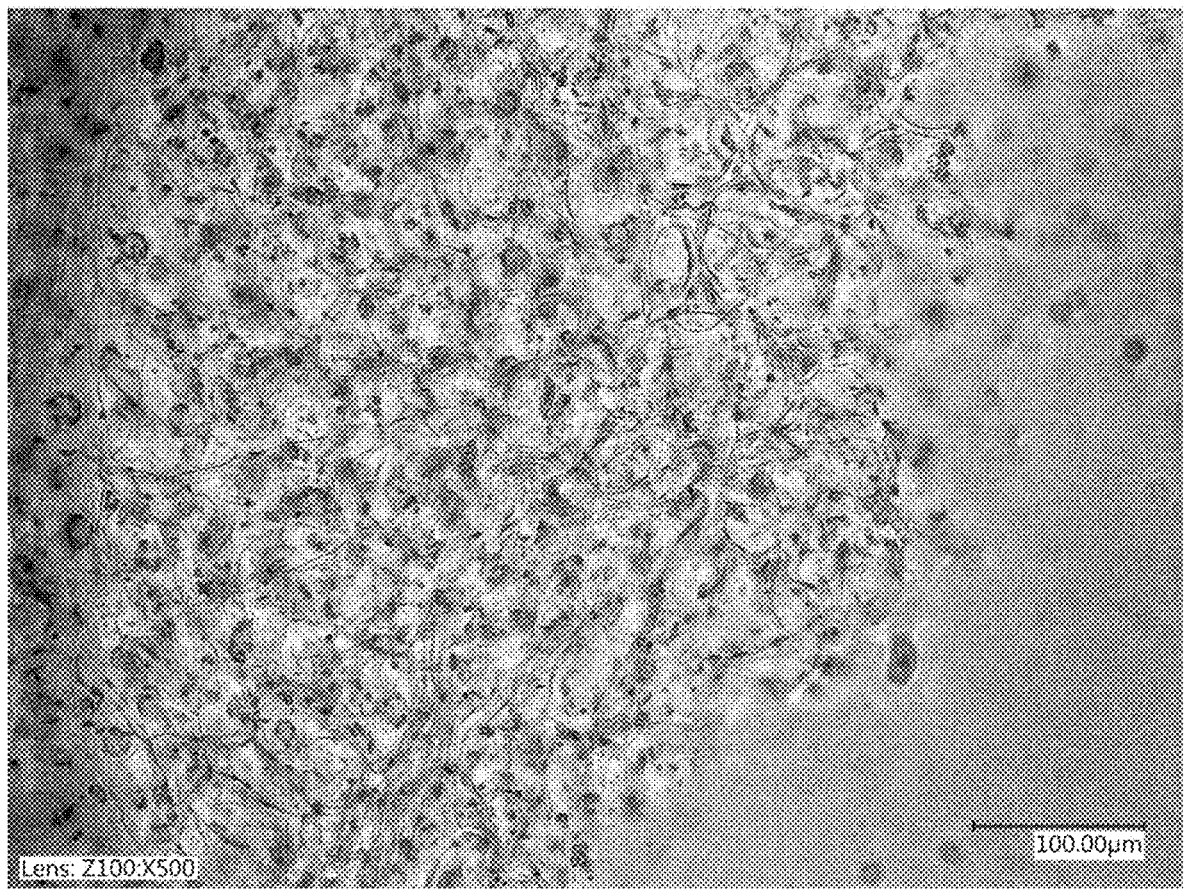
FIG. 5 is an image depicting the sublayer of the cactus skin of OFI at 500× magnification. One can appreciate that areas showing denser regions as sunken or depressed areas. This indicates that smaller polyesters can connect in 3D from one surface region to another, while the larger polyesters are in arranged in a 2D configuration.
Figure 6:
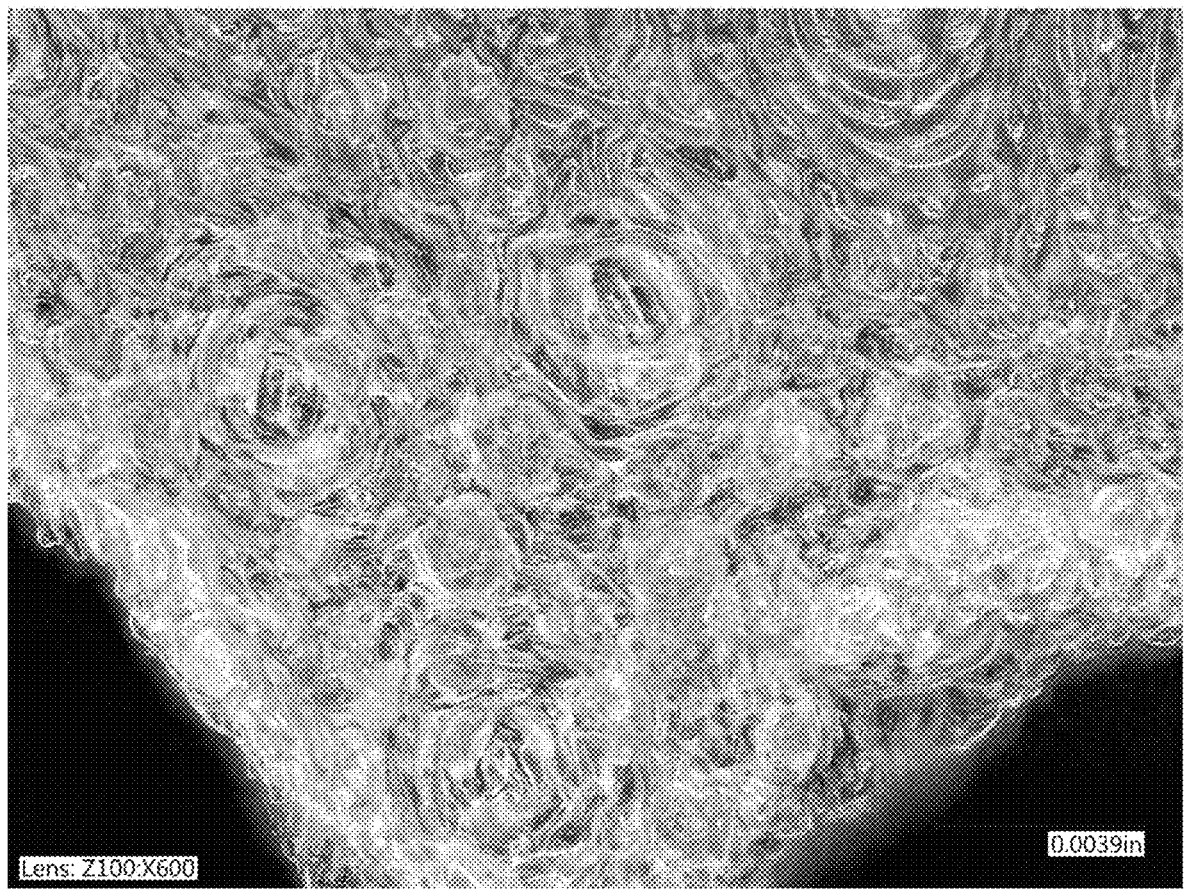
FIG. 6 is an image depicting a closer look at the depressed areas engulfed by the planar layers (600× magnification).
Figure 7:
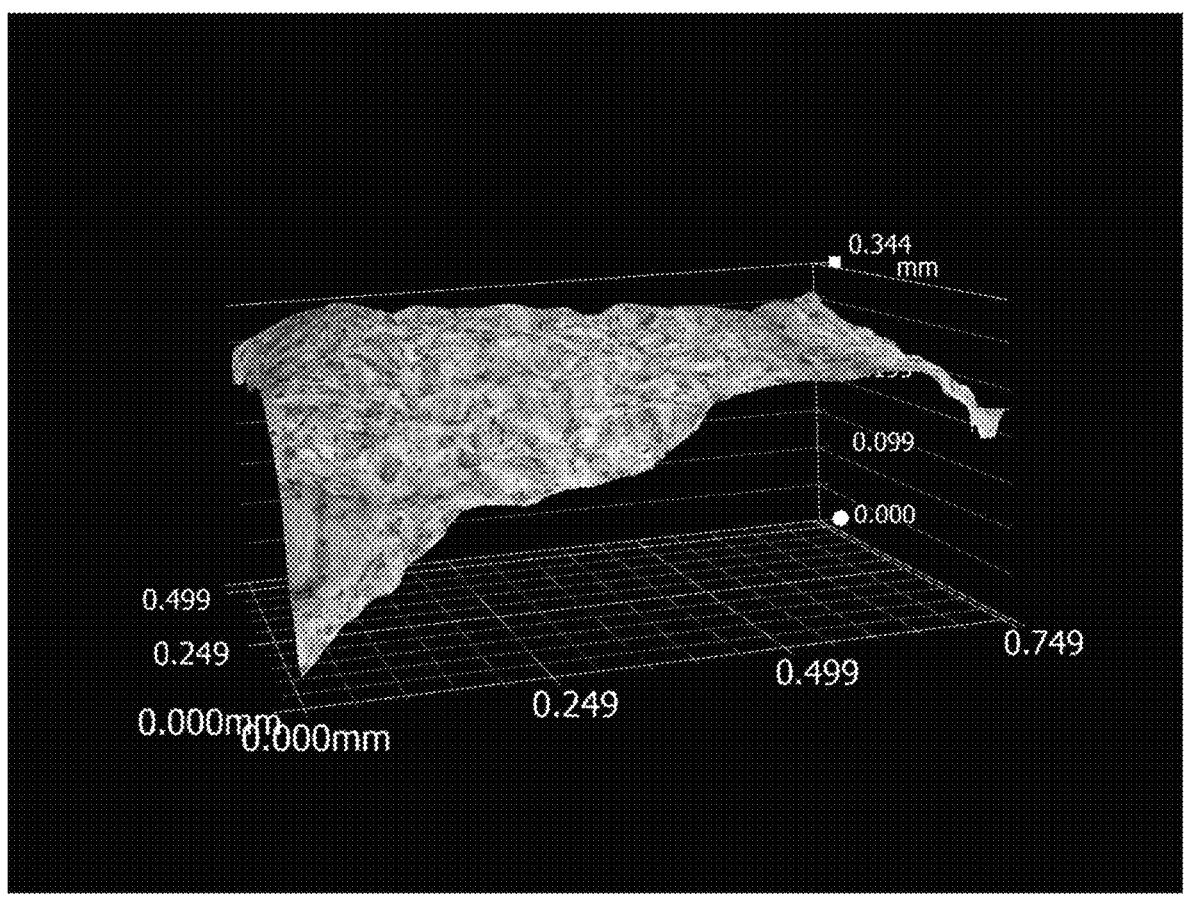
FIG. 7 is an image depicting the depth if the cactus skin (cross-sectional view). One can observe the 3D link between the denser regions (at the edge of the image) confirming that denser areas are arranged in a 3D configuration, while the fibril-like longer polyesters are planar.

The inventors have developed 2-D layered and 3-D structures of CLM coatings and engineered laminates as explained above based on the cutin biopolyesters that have enhanced properties and performance for mechanical, electrical and thermoelectric applications. FIG. 2 shows schematic representations of potential chemical configurations for these long-range 2-D and 3-D cutin-like layers. Briefly, the intermediate oxygen from the end carboxyl group of individual fatty acids stabilizes the growing layer and allows for different crystalline patterns to be formed. Second, 2-D layers are formed using substituted ω-hydroxyl fatty acids in the presence of glycerol or ferulate. By incorporating oxygen rich and aromatic groups, unique paths for electron exchange are formed. Further, the presence of insulating regions, given by the C—C linear regions, leads to enhanced e-transport roadmaps for enhanced electronic activity needed for enriched organic electronics, thermal insulator coatings, and catalysts. Because of the high composition of linear C—C long chains, CLM is much more flexible than any other crystal form of C—C bonds. Such elastic behavior is already seen in natural cutin layer scans under high and low magnification as shown in FIG. 3. Third, addition of fatty acid iron salts in the formation of CLM yields 2-D surfaces with magnetic properties prime to tailor electronic sensitivity. Last, due to the morphology of CLM layers, metallic (e.g., Fe or Au) and dielectric materials (i.e., $SiO_2$ or $Si_3N_4$) can be introduced to the intermediate carboxylic or unsaturated groups of the functionalized fatty acids to enhance surface reactivity and unique reflecting properties. This enhancement is already seen in natural cutin surfaces as shown in the purple domains of this cactus plant grown in silicon dioxide rich soils. With biomimicry as the underlying premise for their synthesis, these novel 2-D and 3-D layered structures have unique capabilities for applications such as flexible electronic devices and large area 2-D laminate structures engineered for unique insulating or conducting capability as well as sensing systems and advanced thermoelectric performance.

These materials can also be modified into emulsions in the food and cosmetic industries to stabilize them and to impart functionality because these molecules have shown amphiphilic characteristics. That is, hydrophobic and hydrophilic groups together are capable of making stable solutions of two substances that would separate into two different phases otherwise. Since the cactus skin is able to resist extreme temperature changes and high energy sun radiation, the cutin-like materials are able to protect biological tissue and surfaces from being degraded, modified, or damaged.

Synthesis of Cutin-Like Precursors

In order to synthesize cutin-like precursors, one must understand how nature is able to design distinct 2-D layered solids based on cutin biopolyesters, not only for developing coatings capable of shielding other surfaces, but also for creating large single crystal arrays subject to chemical, mechanical and electronic functionalization. Coatings can be produced by dipping, spin-coating, electrospinning and surface self-assembly. Large arrays are produced by judiciously controlling synthetic mechanisms of polyesters. The synthesis of monomeric cutin precursors allows the mimicking of nature's ability to recreate the primary aerial surface of cactus plants and one of nature's largest biological interfaces.

2-D and 3-D layered cutin-like materials capable of insulating or conducting, sensing, reacting, as well as displaying mechanical and thermoelectric advance performance, have been developed. The chemical functionalization of precursors and crosslinkers yields composed materials adept at sustaining proper orientation and stacking for higher strength and resilience. CLM layers are highly hydrophobic and impermeable to aqueous media but susceptible to being functionalized in solution making their manufacturing flexible and inexpensive. In addition, CLM generates robust and biologically active substrate platforms with C—C backbones and ester bonding that provide additional surface strength and protection. Cutin surfaces can only be attacked by distinctive biological enzymes. This is the reason why cacti are protected from fungi or plagues. There is only one specific microorganism for each cacti species (with a specific enzyme to break their surface cutin layers to feed and hydrate from their internal pulp) that can cause its death in nature.

The addition of metal and metal oxide compounds during the synthesis of polyesters as described above to cutin-like precursors promotes the formation of electronic bridges or dopants needed for advanced device fabrication with novel magnetic and conducting characteristics. These characteristics are created using compounds such as iron or copper into the polyester chain. The polyester arrays exhibit a new configuration when magnetic fields are applied or they are capable of inducing electron transport. Due to the simple molecular organization that cutin structures have exhibited in nature, the inventors have determined how cutin-like composites can be assembled into nanolayers as a function of precursor type, concentration, and crosslinker ratio to promote defect-free structural anisotropy in 2-D and 3-D layered composites. Several configurations can potentially be explored to induce long-range alignment. These readily available 2-D and 3-D layered composites are well suited for cost effective multifunctional integration into tactical material platforms. That is, these composites can also be incorporated into other surfaces or films via electrospinning, spin-coating or self-assembly.

The synthesis of cutin templates, both aliphatic and aromatic, involve carbon substitution in ω-hydroxy and ω-hydroxy-epoxy unsaturated fatty acids and glycerol. (Li-Beisson, Y. et al., 2009; Kolattukudy, P. E. et al., 2001) This leads to variations of structure and chemical, mechanical and electrical functionality produced by incorporating other groups such as α, ω dicarboxylic acids, fatty alcohols, and ferulate to create polyesters (FIG. 1). Both synthetic (i.e., commercially available polyacids) and naturally extracted cutin precursors were studied. The naturally extraction is performed by dissolving and separating polyesters produced by the cactus plant. In this case, the skin of the pads is removed from flesh and wash with acetone to eliminate chlorophyll. The natural polyesters are then redesolved and separated using centrifugation and purified by high performance liquid chromatography (HPLC).

Ester-bond hydrolysis and transesterification of cuticles from *Opuntia ficusindica* cacti (i.e., OFI or prickly pear) and *Rhipsalis* species (common succulent) yield ferulate, glycerol, and fatty acids and alcohols. (Li, Y. et al., 2007; Pollard, M. et al., 2008) Such cacti have been selected because they are abundant, need little water to growth, are extremely resilient and growth widely. (Barcenas, R. T. et al., 2011; Garcia de Almeida, O. J. et al., 2012; Maffei, M. et al., 1997; Buttice, A. L. et al., 2013; Fox, D. et al., 2012; Pichler, T. et al., 2012) An analysis of benefits and disadvantages of using natural plant versus synthetic precursors will be analyzed and compared using life cycle assessment tools. Other series of experiments involving a 4 point probe will be used to specifically investigate electrical properties of CLM, synthetic fatty acid metal salts (i.e., with iron or copper) and will be compared with the properties of the precursors.

Formation of Arrays of Cutin-like Composites to Create New 2-D Layered Materials In nature, glycerol and oxygen are the main crosslinkers of cutin precursors via ester bonds orchestrated by acid-donor enzymes. The exact mechanism is still unknown. However, Pollard et al., incorporated herein by reference in its entirety, suggested a feasible pathway as described above generally accepted since 2008. (Pollard, M. et al., 2008) Contrary to the heterogeneous cutin natural formation in living plants, synthetic esterification of functionalized fatty acids is well known. (Ahmetli, G. et al., 2012; Allen, D. K. et al., 1999; Corrigan, P. J. et al., 2000; Fang, S. W. et al., 2013; Li, Y. et al., 2009; Xu, J. et al., 2012) In such cases, formation of large areas of 2-D and 3-D layered C—C and ester structures with distinct properties can be attained by using acid- or base catalyzed controlled ratios of cutin precursors in the presence glycerol and oxygen donor groups (FIG. 2). Four configurations were studied.

First, $C_{12}$-$C_{20}$ aliphatic fatty acids link together via esterification resulting in large areas of simple CLM. FIG. 2 illustrates schematic representations of potential chemical configurations for these long-range 2-D cutin-like layers. The intermediate oxygen from the end carboxyl group of individual fatty acids stabilizes the growing layer and allows for different crystalline patterns to be formed.

Second, 2-D layers are formed using substituted ω-hydroxyl fatty acids in the presence of glycerol or ferulate. By incorporating oxygen rich and aromatic groups, unique paths for electron exchange are formed. Further, the presence of insulating regions, given by the C—C linear regions, leads to enhanced electron transport roadmaps for enhanced electronic activity needed for enriched organic electronics, thermal insulator coatings, and catalysts. Because of the high composition of linear C—C long chains, CLM is increasingly more flexible than any other crystal form of C—C bonds. Such elastic behavior is already seen in natural cutin layer scans under high and low magnification as shown in FIG. 3.

Third, addition of fatty acid iron salts in the formation of CLM yields 2-D surfaces with magnetic properties prime to tailor electronic sensitivity.

Last, due to the morphology of CLM layers, metallic (e.g., Fe or Au) and dielectric materials (i.e., $SiO_2$ or $Si_3N_4$) can be introduced to the intermediate carboxylic or unsaturated groups of the functionalized fatty acids to enhance surface reactivity and unique reflecting properties. (Seferos, D. S. et al., 2004; Alcantar, N. A. et al., 2003; Golan, Y. et al., 2000; Alcantar, N. A. et al., 1999) This enhancement is already seen in natural cutin surfaces as shown in the domains of the cactus plant grown in silicon dioxide rich soils (FIG. 3).

These cutin-like advanced materials are functionalized with metals and metal oxides to create enriched nanolayers. The inventors have developed synthesis of cutin-like precursors which lead to the formation of arrays of cutin-like composites to create new 2-D layered materials. The mechanical, physicochemical, thermal, and electronic characterization of cutin-like composites was discovered and cutin-like materials implemented in device fabrication and nanomanufacturing of surfaces and interfaces.

CLM layers are highly hydrophobic and impermeable to aqueous media but susceptible to being functionalized in solution making their manufacturing flexible and inexpensive. In addition, CLM generates robust and biologically active substrate platforms with C—C backbones and ester bonding that can provide additional surface strength and protection. Cutin surfaces can only be attacked by distinctive biological enzymes. (Li, Y. et al., 2007; Gupta, N. S. et al. 2006; Li, Y. et al., 2009) This is the reason why cacti are protected from fungi or plagues. There is only one specific microorganism for each cacti species (with a specific enzyme to break their surface cutin layers to feed and hydrate from their internal pulp) that can cause its death in nature. Specifically, the effect of natural enzymes is used to determine the degree of degradation. Therefore, the team will study specific biodegradation protocols for how these layers render stronger materials yet are decomposable in a control approach making them environmentally benign surfaces, yet difficult to detect or target.

Mechanical, Physicochemical, Thermal, and Electronic Characterization of CLM

The ability to process and coat large areas with a functional and sustainable material typically demands surface preparation prior to coating and the control of the interface parameters to assure intimate and defect-free contact between the cutin-like materials and the substrate. Wetting of the surface and subsequent bonding of the coating is investigated to enhance the ability to create structurally desired coatings by determining advancing and receding contact angles and surface tension measurements with a tensiometer. It has been found that surface preparation methods can reduce the "greenness" of the overall process as demonstrated through environmental impact studies of the pre- and post-processing that may be required. (Wilfong, C. et al., 2012) The level of "greenness" is evaluated with LCA. Surface preparations utilizing biologically acceptable cutin-like substrates that can enhance both the adhesion and protection of the surface underneath are investigated and can be observed in the denser regions of polyesters (FIGS. 4-7). Adhesion can be induced by positioning small polyester molecules in a 3-D configuration. Characterization of the potential substrates such as glass, silicon or metals, prepped surface, coated surfaces, and interfaces are conducted with standard (e.g., spectroscopy, SEM, profilometry, ellipsometry, EDS, XRD and ATM) methods and unique accelerated life tests (e.g. microprofiling, 4-point bend tests, SFA, nanoscratch). In particular, protocols are developed to determine and optimize the relationships between design parameters for CLM, such as precursor type, fatty acid concentration, solvent, and crosslinker ratio, and their functionality, which include gel permeation chromatography and HPLC. Electronic characterization of the 2-D and 3-D CLM nanolayers is conducted through current-voltage (I-V), resistivity, electrochemical impedance spectroscopy (EIS) and cyclic voltammetry (C-V) methods using a 4-probe conductimeter. It is expected that these surfaces will exhibit photoreactivity because optical reflections have been observed when the cutin layers are exposed to white light (FIG. 3). The thermal behavior of these layers will be analyzed by inducing heating cycles (temperature ramps from −20 to 350° C. with time durations), and to evaluate dilation and robustness using optical microscopy.

Implementation of CLM in Device Fabrication and Nanomanufacturing of Surfaces and Interfaces Once large areas of CLM are constructed and characterized individually, their implementation as sensors and electronic devices is assessed. An advantage of using cutin-like materials is that density and fluidity can also be constructed on demand by assembling of individual blocks of these layers, specialized for a large number of applications, including 2-D and 3-D scaffolds for catalytically reactive surfaces as well as flexible surfaces, and as templates for biological applications. The sustainability of the research is enhanced by the natural biochemical process that nature uses to synthesize cutin in cacti. In particular, CLM has high impact for Air Force Office of Scientific Research (AFOSR) challenges where large areas of low density, crystalline surfaces can be used as protective coatings for aircraft infrastructure. Similarly, surfaces with distinct electronic and magnetic properties are relevant to device nanomanufacturing and sensing/detecting in the design of the next generation of flying machinery and military armor. Direct measurements of frequency response as a function of precursor type, surface structure, and assembly using electrochemical impedance spectroscopy determines how stable and electronically robust these organic electronics can be and the protocols for their implementation.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of manufacturing cutin-like materials (CLM) for use in two-dimensional coatings and three-dimensional structures comprising:
   providing CLM precursors in a solution;
   adding substituted w-hydroxyl fatty acids to the solution;
   adding glycerol or ferulate to the solution; and
   adding an acid or base to the solution to catalyze a reaction between oxygen donor groups, the glycerol and the CLM precursors;
   wherein the reaction promotes formation of CLM.

2. The method of claim 1, wherein the CLM precursors are naturally derived.

3. The method of claim 2, wherein the CLM precursors are derived from cutin found in cacti species selected from the group consisting of *Opuntia ficus-indica, Agave Americana, Cereus peruvianus*, and *Rhipsalis* species.

4. The method of claim 1, wherein the CLM precursors are synthetically derived.

5. The method of claim 1, wherein the CLM precursors are $C_{12}$-$C_{20}$ aliphatic fatty acids.

6. The method of claim 5, wherein the aliphatic fatty acids are linked together via esterification to result in areas of CLM.

7. The method of claim 1, further comprising incorporating fatty acid iron or copper salts into the solution.

8. The method of claim 1, further comprising incorporating metallic and dielectric materials into the solution to enhance surface reactivity and reflecting properties of the CLM.

9. The method of claim 8, wherein the metallic materials are selected from the group consisting of iron (Fe) and gold (Au).

10. The method of claim 8, wherein the dielectric materials are selected from the group consisting of silicon dioxide ($SiO_2$) and silicon nitride ($Si_3N_4$).

* * * * *